(12) United States Patent
Hsia et al.

(10) Patent No.: US 8,712,760 B2
(45) Date of Patent: Apr. 29, 2014

(54) METHOD AND MOBILE DEVICE FOR AWARENESS OF LANGUAGE ABILITY

(75) Inventors: Chi-Chun Hsia, Kaohsiung (TW); Yu-Hsien Chiu, Kaohsiung County (TW); Wei-Che Chuang, Kaohsiung (TW); Kuo-Yuan Li, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 393 days.

(21) Appl. No.: 12/981,042

(22) Filed: Dec. 29, 2010

(65) Prior Publication Data

US 2012/0053929 A1 Mar. 1, 2012

(30) Foreign Application Priority Data

Aug. 27, 2010 (TW) .............................. 99128768 A (51) Int. Cl.
*G06F 17/27* (2006.01)
*G10L 15/01* (2013.01)

(52) U.S. Cl.
USPC .............................................. 704/9; 704/271

(58) Field of Classification Search
CPC ................................. G10L 15/01; G06F 17/27
USPC ..................................................... 704/9, 271
See application file for complete search history.

(56) References Cited

U.S. PATENT DOCUMENTS

| | | | |
|---|---|---|---|
| 4,284,846 A | 8/1981 | Marley | |
| 4,637,007 A | 1/1987 | Sakurai | |
| 4,720,862 A | 1/1988 | Nakata et al. | |
| 4,783,807 A | 11/1988 | Marley | |
| 5,082,446 A | 1/1992 | Sclan et al. | |
| 5,230,629 A | 7/1993 | Buschke | |
| 5,601,432 A | 2/1997 | Bergman | |
| 5,974,413 A * | 10/1999 | Beauregard et al. | ............. 1/1 |
| 6,157,911 A | 12/2000 | Kuroda | |
| 6,711,541 B1 | 3/2004 | Kuhn et al. | |
| 6,796,799 B1 | 9/2004 | Yoshiike et al. | |
| 6,820,056 B1 | 11/2004 | Harif | |
| 6,829,582 B1 | 12/2004 | Barsness | |
| 6,999,923 B1 | 2/2006 | Ablondi et al. | |

(Continued)

FOREIGN PATENT DOCUMENTS

CN 1655235 8/2005

OTHER PUBLICATIONS

An Overview of Automatic Speaker Diarization Systems Sue E. Tranter, and Douglas A. Reynolds IEEE Transactions on Audio, Speech, and Language Processing Sep. 2006.

(Continued)

*Primary Examiner* — David Hudspeth
*Assistant Examiner* — Timothy Nguyen
(74) *Attorney, Agent, or Firm* — WPAT, PC; Justin King (57) ABSTRACT

A method and mobile device for awareness of language ability are provided. "Repeated pattern index"-related properties, such as, a vocabulary usage amount, a vocabulary type, or a ratio, a time point, a time length or repeated contents of a repeated voice segment, and "community interaction index"-related properties, such as, a number of persons who speak with a user, a conversation time length, or whether the user talks alone during each time interval, are extracted according to voice data collected by a voice collection element worn on the user. Then, a language ability of the user is further calculated, so as to provide evaluation of the language ability of a dementia patient for reference.

7 Claims, 5 Drawing Sheets

(56) References Cited

U.S. PATENT DOCUMENTS

| | | | |
|---|---|---|---|
| 7,008,378 | B2 | 3/2006 | Dean |
| RE39,090 | E * | 5/2006 | Beauregard et al. .................. 1/1 |
| 7,128,651 | B2 | 10/2006 | Miyamoto et al. |
| 7,143,044 | B2 * | 11/2006 | Zadrozny et al. ............. 704/275 |
| 7,177,806 | B2 | 2/2007 | Washio |
| 7,187,790 | B2 | 3/2007 | Sabol et al. |
| 7,231,019 | B2 * | 6/2007 | Pascovici .................. 379/88.02 |
| 7,337,115 | B2 * | 2/2008 | Liu et al. ....................... 704/246 |
| 7,505,911 | B2 | 3/2009 | Roth et al. |
| 7,567,676 | B2 | 7/2009 | Griesinger |
| 7,567,693 | B2 | 7/2009 | deCharms |
| 7,682,308 | B2 | 3/2010 | Hendrich |
| 7,684,988 | B2 * | 3/2010 | Barquilla .................. 704/256.1 |
| 7,711,578 | B2 | 5/2010 | Williams et al. |
| 7,715,387 | B2 | 5/2010 | Schuman |
| 7,729,907 | B2 | 6/2010 | Rikimaru |
| 7,818,179 | B2 * | 10/2010 | Krasikov et al. ............. 704/274 |
| 7,912,705 | B2 * | 3/2011 | Wasson et al. ..................... 704/9 |
| 8,265,724 | B2 * | 9/2012 | Petersen ....................... 600/331 |
| 2002/0156774 | A1 * | 10/2002 | Beauregard et al. ............. 707/3 |
| 2003/0101053 | A1 | 5/2003 | Washio |
| 2005/0076771 | A1 * | 4/2005 | Carlson ........................... 84/613 |
| 2005/0108017 | A1 * | 5/2005 | Esser et al. .................... 704/277 |
| 2006/0031071 | A1 * | 2/2006 | Abrego et al. ................ 704/256 |
| 2006/0239471 | A1 | 10/2006 | Mao et al. |
| 2007/0156401 | A1 | 7/2007 | Nagano et al. |
| 2007/0191725 | A1 | 8/2007 | Nelson |
| 2007/0256499 | A1 | 11/2007 | Pelecanos et al. |
| 2008/0025477 | A1 | 1/2008 | Farhan |
| 2008/0276790 | A1 | 11/2008 | Lemons |
| 2009/0099848 | A1 * | 4/2009 | Lerner et al. .................. 704/271 |
| 2009/0163779 | A1 | 6/2009 | Dean |
| 2009/0210223 | A1 | 8/2009 | Kim |
| 2010/0100036 | A1 * | 4/2010 | Leuthardt et al. ............... 604/65 |
| 2012/0020505 | A1 * | 1/2012 | Yamada et al. ................ 381/313 |
| 2012/0197153 | A1 * | 8/2012 | Kraus et al. ................... 600/545 |

OTHER PUBLICATIONS

Combining Speaker Identification and BIC for Speaker Diarization Xuan Zhu, Claude Barras, Sylvain Meignier and Jean-Luc Gauvain Proceeding of Interspeech'2005—Eurospeech—9th European Conference on Speech Communication and Technology Sep. 2005.

Never-Ending Learning System for On-Line Speaker Diarization Konstantin Markov1 and Satoshi Nakamura1 Proceeding of 2007 IEEE Automatic Speech Recognition and Understanding Workshop Dec. 2007.

A Study on Synthesis Unit Selection and Voice Conversion for Text-to-Speech Synthesis Hsia, Chi-Chun Dec. 2007.

Taiwan office action issued on Mar. 19, 2013.

* cited by examiner

METHOD AND MOBILE DEVICE FOR AWARENESS OF LANGUAGE ABILITY

BACKGROUND OF THE DISCLOSURE

1. Field of Disclosure

The present disclosure relates to awareness of language ability, and more particularly to a method and mobile device for awareness of language ability.

2. Related Art

Statistics indicate that the number of elderly dementia patients over the world will exceed 35 million in 2010. Dementia is undoubtedly a severe social problem. Dementia is not incurable, and among the elderly dementia patients, about 10% can be cured; 35% suffer from vascular dementia caused by cerebral apoplexy, which can be inhibited or alleviated through therapy; and 55% suffer from deteriorating Alzheimer's disease, which can still be treated.

Symptoms of the dementia patients are not only reflected in forgetfulness, misidentification, emotional change, or getting lost, but also reflected in the ability of language expression and degree of community participation requiring interaction with others. Gulay Sezgin, chief physician of the Alzheimer's Disease Treatment Centre in Ankara, the capital of Turkey, pointed out that: "The elderly should keep contact with the outside world, so as to increase the brain excitation opportunity and prevent brain cells from stasis and aging."

Since memory degrades, and the dementia patients often forget things done or words said, they will do some repeated actions or constantly repeat some sentences. The symptom of "repeating a same question, story, and statement" is also listed in evaluation items of a very early dementia screening scale (AD8).

The evaluation of dementia is largely dependent upon a scale, such as a Mini-Mental Status Examination (MMSE), and common questions include, for example, "What date is today?", "Which year is this year?", and "Which county and city are you in?"; or, the questions about number recognition, for example, a subject is asked to gradually read the numbers from 100 minus 7: 100, 93, 86, 79, 72 . . . . Regarding the evaluation of very early dementia, so-called key evaluation items of the very early dementia scale (AD8) exist, including 1.) repeated statement: a frequency of occurrence, a time point, a time length, and contents; 2.) soliloquy: a frequency of occurrence, a time point, and a time length; and 3.) having conversation with how many people: whether the people talk to the subject is becoming less and less; and all the above evaluation items can be known by analyzing records of daily conversation of the subject, and it is difficult to express the symptoms by evaluation using a simple scale.

SUMMARY OF THE DISCLOSURE

Accordingly, the present disclosure is directed to a method and mobile device for awareness of language ability, which can implement mobile speech collection and further analyze a language ability state of an observed person, so as to provide evaluation of language ability-related symptoms (including dementia).

The present disclosure provides a method and mobile device for awareness of language ability. The device comprises: an analysis platform; a voice collection element, electrically connected to the analysis platform, for collecting required voice data; and a language ability evaluation unit, embedded in the analysis platform, or electrically connected to the analysis platform, wherein the language ability evaluation unit receives the voice data collected by the voice collection element, evaluates and calculates a language ability, and outputs an evaluation result.

The method comprises: an audio processing step, wherein after a voice is received by a voice collection element, a voice activity detection module in a language ability evaluation unit extracts a voice segment with speech sound from the voice, and a feature extraction module in the language ability evaluation unit calculates a feature vector sequence of the voice segment, that is, extracts a voice segment feature vector for analysis; a repeated pattern index estimating step, wherein a steady state voice segment detection and quantization module in the language ability evaluation unit directly obtains a codeword sequence, a repeated voice segment detection module in the language ability evaluation unit performs a repeated voice segment matching algorithm, so as to determine whether the codeword sequence contains one or at least one repeated voice segment, and not only a full-domain language model is established based on codewords of common daily expressions, but also a catching language model is established based on codewords that occur recently, which are used in repeated voice segment matching, so as to obtain a repeated pattern index; and a community interaction index estimating step, wherein a speaker diarization module in the language ability evaluation unit detects a speaking time/times ratio of speakers, a conversation time length, and a speaker alternation times, and even detects whether a phenomenon of soliloquy exists, so as to obtain a community interaction index.

Therefore, the speech of the user and the person speaks to the user is received by the mobile voice collection element, and then, the "repeated pattern index" and the "community interaction index" of the user are analyzed; the language ability evaluation unit is embedded in the analysis platform, or is electrically connected to the analysis platform, in which the repeated pattern index may be the ratio, the time point or the time length of the repeated voice segment, and the community interaction index may be a number of persons who speak with the user, a conversation time length, or whether the user talks alone (that is, soliloquy) during each time interval.

BRIEF DESCRIPTION OF THE DRAWINGS

The present disclosure will become more fully understood from the detailed description given herein below for illustration only, and thus are not limitative of the present disclosure, and wherein.

DETAILED DESCRIPTION OF THE DISCLOSURE

The present disclosure is described through several embodiments, however, the accompanying drawings and specific embodiments are merely embodiments of the present disclosure. It should be noted that, the specific embodiments disclosed below are merely examples of the present disclosure, and the present disclosure is not limited to the accompanying drawings and the specific embodiments.

Figure 1:
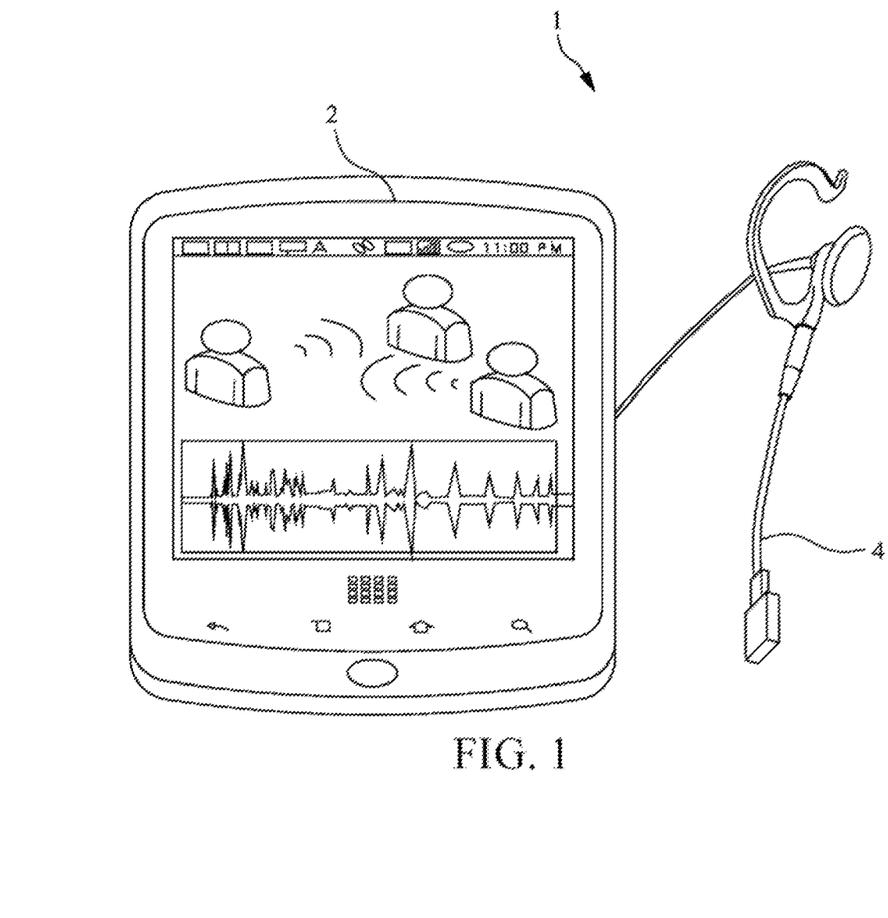
FIG. 1 is an outside view of a mobile device for awareness of language ability according to the present disclosure.

FIG. 1 is an outside view of a mobile device for awareness of language ability according to the present disclosure. Referring to FIG. 1, the mobile device for awareness of language ability 1 of the present disclosure has a voice collection element 4 capable of adjusting a voice-receiving position, such as a microphone. A language ability evaluation unit 3 is built inside an analysis platform 2, and is portable so as to evaluate the language ability of a detected person in real time. The mobile voice collection element 4 of the microphone receives voice data of a user and a person speaks to the user, and then analyzes a "repeated pattern index" and a "community interaction index" of the user. The language ability evaluation unit 3 is embedded in the analysis platform 2 such as an embedded system, or may be electrically connected to the analysis platform 2 such as a personal computer (PC).

Community Interaction Index Estimation

The community interaction index may be calculated according to one or more of the following properties: a number of persons who speak with the user, a conversation time length, and whether the user talks alone during each time interval.

Gulay Sezgin, chief physician of the Alzheimer's Disease Treatment Centre in Ankara, the capital of Turkey, pointed out that: "The elderly should keep contact with the outside world, so as to increase the brain excitation opportunity and prevent brain cells from stasis and aging." In other words, a community interaction ability of the elderly is also an important index for preventing or detecting dementia. Conversation objects of the elderly may be diarized by using a voice sensor in combination with a speaker diarization technology, and community interaction-associated evaluation may be performed based on the number of conversation objects.

Figure 2:
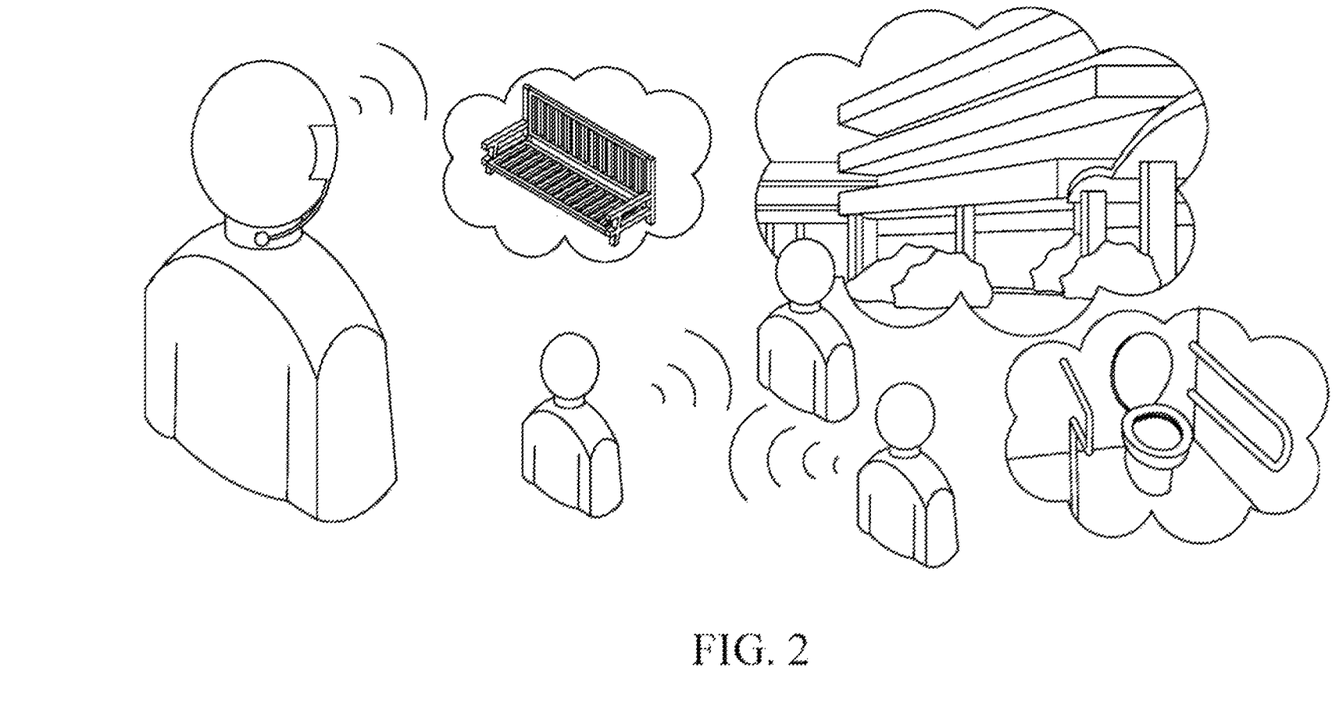
FIG. 2 is a schematic view of a multi-person conversation situation.

FIG. 2 is a schematic view of a multi-person conversation situation. The user may have a conversation in an indoor public space, or may gather and chat at an outdoor arcade or a resting place. Thus, the degree of social participation of a possible dementia patient can be assessed according to a conversation amount including conversation objects, number of people, time or time length, and degree of participation (speaking time). In addition, some regressed dementia patients may have a symptom of soliloquy, and they may talk alone on a chair and even in a washroom.

Repeated Pattern Index Estimation

The repeated pattern index may be calculated according to one or more of the following properties: a ratio, a time point, a time length and repeated contents of a repeated voice segment.

Method Flow

Figure 3:
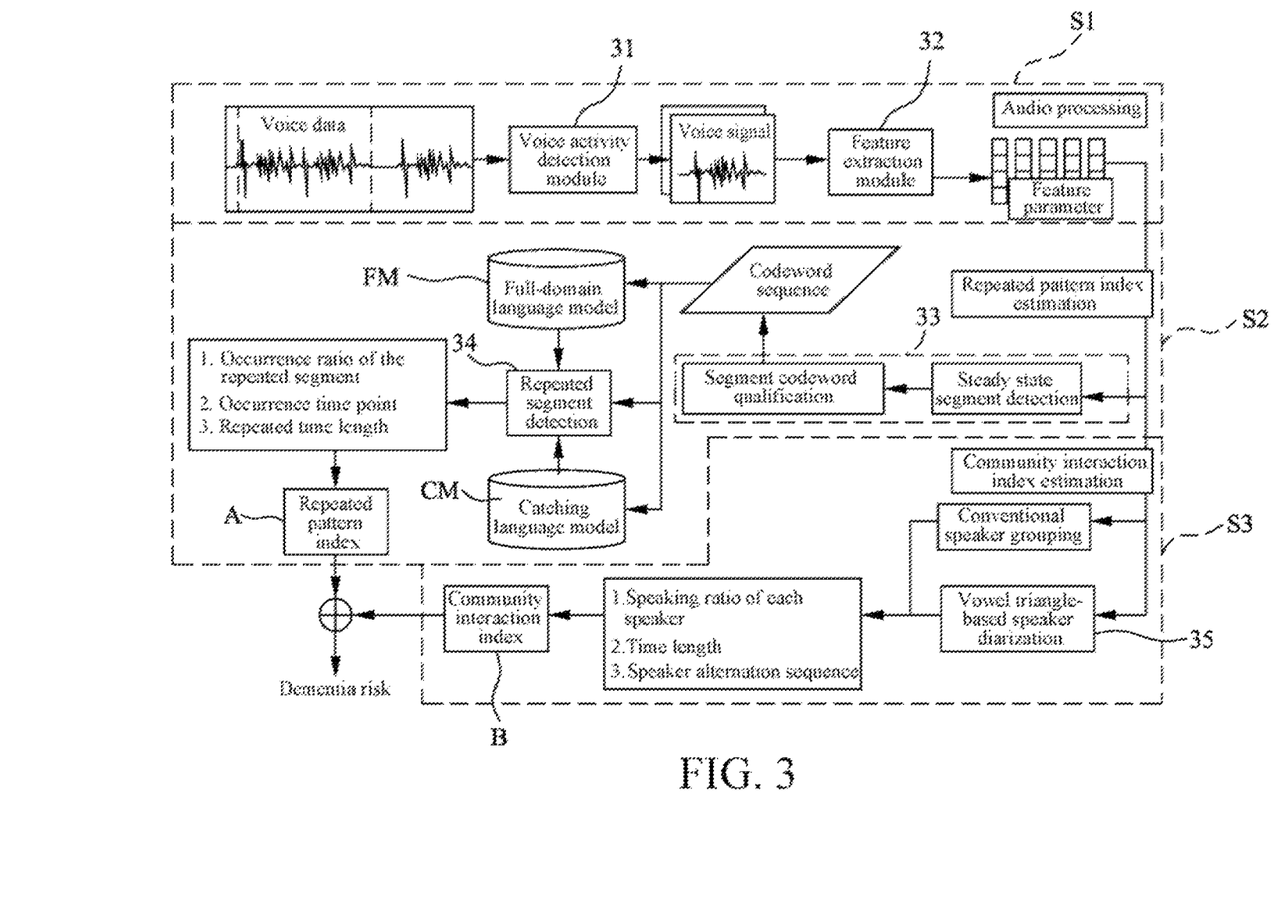
FIG. 3 is a flow chart of a method for awareness of language ability according to the present disclosure.

FIG. 3 is a flow chart of a method for awareness of language ability according to the present disclosure. The method for awareness of language ability of the present disclosure includes the following steps.

In Step S1: an audio processing step is performed. After a voice is received, and before subsequent language ability property estimating steps (Steps S2 and S3) are performed, it is necessary to perform the audio processing step (Step S1) first, in which a voice activity detection module 31 extracts a voice segment with speech sound, and a feature extraction module 32 calculates a feature vector sequence of the voice segment, that is, extracts a voice segment feature vector for analysis. Finally, a "repeated pattern index" and a "community interaction index" respectively produced in Step S2 and Step S3 may be respectively estimated according to a plurality of language ability properties.

In Step S2: a repeated pattern index estimating step is performed. In the repeated pattern index estimating method of the present disclosure, it may not need to analyze speech text contents through conventional large vocabulary speech recognition and keyword detection. Instead, a steady state voice segment detection and quantization module 33 directly quantizes a voice segment codeword, so as to obtain a codeword sequence. A repeated voice segment matching part uses a repeated voice segment detection module 34 with a codeword catching n-gram model to determine whether the codeword sequence contains a repeated voice segment. Not only a full-domain language model FM is established based on codewords of common daily expressions, but also a catching language model CM is established based on codewords that occur recently, which are used in repeated voice segment matching, so as to obtain a repeated pattern index A. Although a vocabulary meaning cannot be recognized by this method, messages such as a repetition ratio, a repetition time point, and time length of the conversation can still be evaluated.

In Step S3: a community interaction index estimating step is performed. The community interaction index estimation may be performed through conventional speaker grouping, speaker recognition and speaker identification, or a speaker diarization module 35 of a vowel triangle-based method according to the present disclosure detects a speaking time/times ratio of speakers, a conversation time length, and a speaker alternation times, and even detects whether a phenomenon of soliloquy exists, so as to obtain a community interaction index B. The diarization method of the speaker diarization module based on the vowel triangle will be described in detail hereinafter.

Device Architecture

Figure 4:
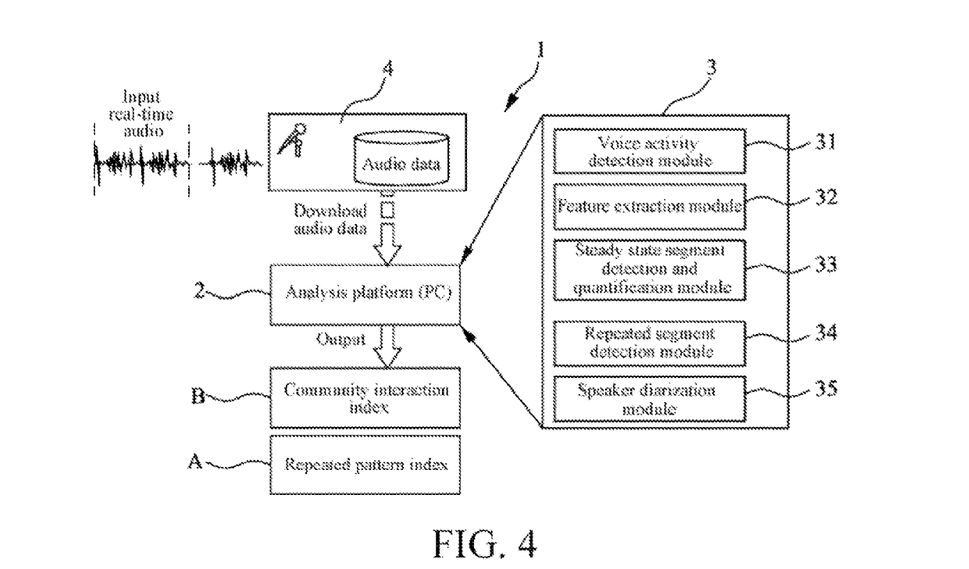
FIG. 4 illustrates a device architecture when a personal computer (PC) is taken as an analysis platform according to the present disclosure.
Figure 5:
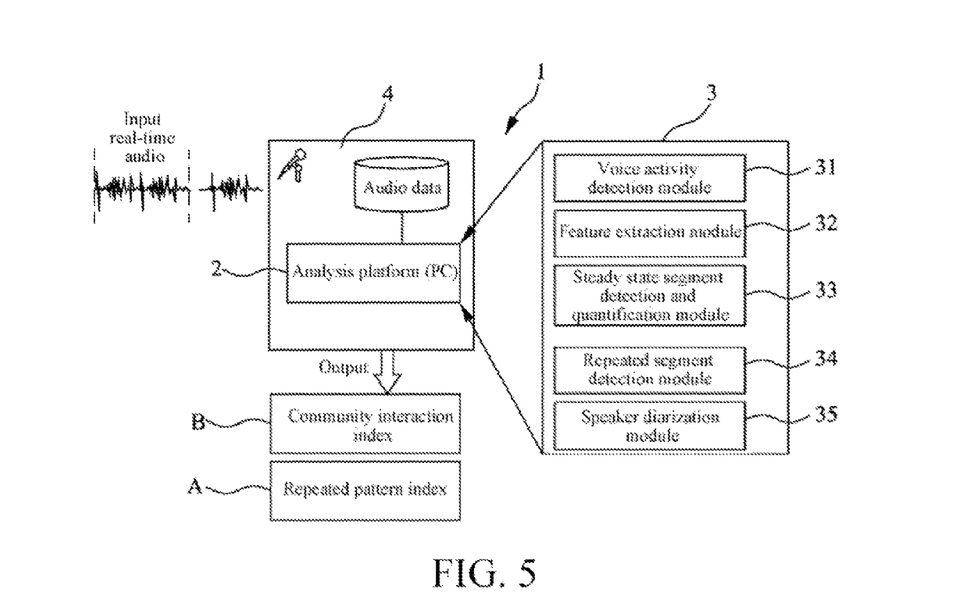
FIG. 5 illustrates a device architecture when an embedded system is taken as an analysis platform according to the present disclosure.

The mobile device for awareness of language ability 1 of the present disclosure includes an analysis platform 2, a language ability evaluation unit 3, and a voice collection element 4. The language ability evaluation unit 3 is embedded in the analysis platform 2 such as an embedded system, or may be electrically connected to the analysis platform 2 such as a PC. FIG. 4 and FIG. 5 respectively illustrate device architectures when the PC is taken as the analysis platform and when the embedded system is taken as the analysis platform.

The voice collection element 4 may sense voice signals of or near a wearer. The voice collection element 4 may be a portable device, such as a recorder pen, a smart phone, a personal digital assistant (PDA), or other handheld or wearable voice collection devices. Collected voice data may be analyzed by the language ability evaluation unit 3 in the analysis platform 2, and then, the community interaction index A and the repeated pattern index B are output by the above method for awareness of language ability of the present disclosure.

The language ability evaluation unit 3 further includes a voice activity detection module 31, a feature extraction module 32, a steady state voice segment detection and quantization module 33, a repeated voice segment detection module 34, and a speaker diarization module 35. The voice activity detection module 31 extracts a voice segment with speech sound. The feature extraction module 32 receives the voice data input by the voice collection element 4, and estimates a speech parameter, including a frequency cesptrum coefficient, a line spectral pair coefficient, a pitch, a sound intensity, and a voice segment length. The steady state voice segment detection and quantization module 33 quantizes the voice segment codeword to obtain a codeword sequence. The repeated voice segment detection module 34 detects a repeated voice segment in the voice data, outputs a voice of the repeated voice segment and calculates an occurrence ratio of the repeated voice segment, an occurrence time point, a repetition time length, or literal contents of the repeated voice segment. The speaker diarization module 35 analyzes a speaker number, a speaking ratio of each speaker, a time length, or a speaker alternation sequence in speech data of a conversation through a speaker diarization method. In addition, the related functions among the elements are as described in the above method for awareness of language ability, so that the details will not be described herein again.

Further, a vocabulary ability evaluation module may be further included (not shown), which may detect and output a vocabulary usage amount, a vocabulary type, or a ratio, a time point, a time length or repeated contents of a repeated voice segment through vocabulary recognition or continuous speech recognition.

Community Interaction Index Estimation Using Speaker Diarization

The vowel triangle-based method of the present disclosure for performing the speaker diarization includes the following steps. Before speaker clustering is performed, it is necessary to find a feature value of the speaker voice in a time domain or a frequency domain, quantization and modeling are performed by using a probability model such as a Gaussian mixture model (GMM) according to the feature value, and then diarization is performed. In the present disclosure, two feature extraction methods, namely, formants estimation and Mel-Frequency Cesptrum Coefficients, are adopted, which are respectively described hereinafter.

a. Formants Estimation

The voice is generated by resonance through a sound track from a sound source. The sound track refers to a cavity from the vocal cord up to the lips (including nasal cavity), and this region is a resonant cavity of the voice. A position where the voice of a person generates centralized energy on a frequency domain is referred to as a formant. As different resonant cavities and vocalizations of vowels cause different formants, differences between speakers may be categorized for diarization. As regards the formants estimation, an all-pole signal model is firstly adopted, and polar coordinates on a unit circle of a polar coordinate plane are estimated through a Levinson-Durbin recursion algorithm. An equation of the all-pole signal model is as follows:

$$H_i(z) = \frac{1}{1 - 2re^{j\omega_i}z^{-1}} \quad (1)$$

The polar coordinates on the unit circle are represented by ($\cos \omega_i$, $i \sin \omega_i$), and corresponding formant frequency $F_i$ and bandwidth $FB_i$ are obtained according to Equations (2) and (3):

$$F_i = \frac{\omega_i}{2\pi} F_s \quad (2)$$

$$FB_i = \cos^{-1}\left(\frac{4r - 1 - r^2}{2r}\right)\frac{F_s}{\pi} \quad (3)$$

$F_s$ represents a sampling frequency of the voice signal.

Figure 6:
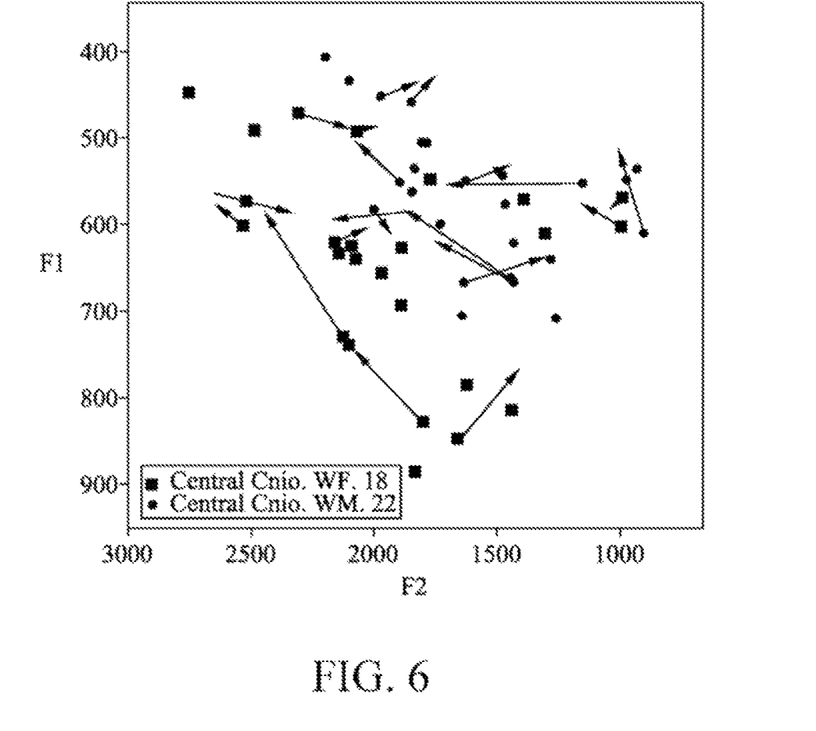
FIG. 6 illustrates differences of male and female speakers presented on a vowel triangle according to the present disclosure.

FIG. 6 illustrates differences of male and female speakers presented on a vowel triangle according to the present disclosure, in which WM represents vowel formant dispersion of male speakers, and WF represents vowel formant dispersion of female speakers.

b. Mel-Frequency Cesptrum Coefficients

The auditory sensation of human ears is more sensitive to low-frequency part than high-frequency part. The Mel-Frequency Cesptrum Coefficient is a voice feature coefficient designed according to the auditory scale of human ears, and is one of the most common feature parameters for speech recognition.

Repeated Pattern Extraction Using Codeword Matching

Since memory degrades, and the dementia patients often forget things done or words said, they will do some repeated actions or repeat some sentences. The symptom of "repeating a same question, story, and statement" is also listed in evaluation items of a very early dementia screening scale (AD8). Therefore, a ratio, a time point and a time length of a repeated voice segment by a patient during conversation or statement may be used as evaluation indices of dementia.

a. Codeword Encoding for Homogeneous Voice Segments

Considering equipment cost and machine performance, in the repeated voice segment matching algorithm, the complex large vocabulary speech recognition technology is not used, and instead, a simple acoustic model established on a Semi-Hidden Markov Model (Semi-HMM) is used. Voice segment division and codeword encoding are directly performed for homogeneous voice segments on a time axis. In order to avoid the time-consuming optimal path searching and decoding process during the speech segment recognition, a state number of the Semi-HMM in the present disclosure is set as 1, and length features of the voice segments are described by using a duration model. A single state design is adopted to avoid the time-consuming HMM decoding. In addition, properties of the voice segment length can be maintained through the duration model.

$$P_i(x_{t-\tau+1}; x_t, \tau) = d_i(\tau)O_i(x_{t-\tau+1} : x_t; \Lambda_i) \quad (4)$$

$$= N_i(\tau; \overline{\mu}_i, \overline{\sigma}_i^2)\left(\prod_{s=t-\tau+1}^{t} \sum_{j=1}^{M} \omega_{i,j} N(x_s; \mu_{i,j}, \Sigma_{i,j})\right)$$

1. $x_t$, a speech feature vector at a time point t, unit: frame.
2. $x_{t-\tau+1}:x_t$ a speech feature vector sequence from time points t−τ+1 to t.
3. τ: voice segment length
4. $P_i(x_{t-\tau+1}:x_t,\tau)$: an observation probability in an $i^{th}$ state of the speech feature vector sequence $x_{t-\tau+1}:x_t$ with the length τ.
5. $d_i(\tau)$: a duration probability of consecutive τ frames in the $i^{th}$ state.
6. $O_i(x_{t-\tau+1}:x_t;\Lambda_i)$: a total observation probability of the speech feature vectors $x_{t-\tau+1}, \ldots, x_t$ in the $i^{th}$ state.
7. $d_i(\tau)=N_i(\tau;\overline{\mu}_i,\overline{\sigma}_i^2)$: the duration probability represented through normal distribution, where $\overline{\mu}_i$ is an average value of duration lengths in the $i^{th}$ state, unit: frame, and $\overline{\sigma}_i^2$ is a variance thereof.

It is assumed that the speech feature vectors are independent, it can be obtained that the total observation probability is a product of the observation probabilities, as shown in the following equation:

$$O_i(x_{t-\tau+1}:x_t;\Lambda_i)=\Pi_{s=t-\tau+1}^{t}O_i(x_s;\Lambda_i)$$

where $\Lambda_i$ is a probability model parameter in the $i^{th}$ state.

The observation probability of each speech feature vector in the $i^{th}$ state is represented by using the GMM:

$$O_i(x_s;\Lambda_i)=\Sigma_{j=1}^{M}\omega_{i,j}N(x_s;\mu_{i,j},\Sigma_{i,j})$$

1. M is a number of Gaussian mixtures.
2. $\mu_{i,j}$ is a weight of the $j^{th}$ Gaussian in the $i^{th}$ state.

3. $\omega_{i,j}$ is an average vector of the $i^{th}$ Gaussian in the $i^{th}$ state.

4. $\Sigma_{i,j}$ is a covariance matrix of the $j^{th}$ Gaussian in the $i^{th}$ state.

b. Codeword Language Model

Possible repeated similar homogeneous voice segment codewords may be obtained by matching for different speech segments. In order to match the repeated voice segment quickly, in the present disclosure, the speech recognition is not adopted, and vocabulary or semantic analysis is not processed, either. The present disclosure focuses on repeated occurrence of the homogeneous voice segment codeword, that is, extraction of similar codeword sequences. Therefore, a connection and combination situation among codewords is described by using a codeword n-gram model in the present disclosure. A voice segment codeword rather than a conventional Chinese vocabulary is taken as a basic element in the model, so that the complex speech recognition and even a large amount of calculation required by multi-language recognition can be avoided. In order to detect the voice segment that is usually repeated by the patient recently, a catching model is further introduced in the present disclosure, so that the codeword language model has an effect of time memory.

$$\overline{P}(V_i \mid V_{i-2}V_{i-1}) \approx \lambda \frac{C(V_i \mid V_{i-2}V_{i-1})}{C(V_{i-2}V_{i-1})} + (1-\lambda)\frac{C(V_i \mid V_{i-1})}{C(V_{i-1})} \quad (5)$$

$$P(V_i \mid V_{i-2}V_{i-1}) = \overline{P}(V_i \mid V_{i-2}V_{i-1}) + P_{catching}(V_i \mid V_{i-2}V_{i-1}) \quad (6)$$

1. $V_i$ represents a codeword of an $i^{th}$ voice segment after quantization.

2. $P(V_i|V_{i-2}V_{i-1})$ represents a probability of occurrence of $V_i$ after $V_{i-2}V_{i-1}$ is given, and is obtained by combining probabilities of two parts:

$$P(V_i|V_{i-2}V_{i-1}) = \overline{P}(V_i|V_{i-2}V_{i-1}) + P_{catching}(V_i|V_{i-2}V_{i-1}).$$

3. $\overline{P}(V_i|V_{i-2}V_{i-1})$ represents a probability obtained based on data previously accumulated for a long time, and is obtained by bi-gram and uni-gram adjusting the weight in a linear manner:

$$\overline{P}(V_i \mid V_{i-2}V_{i-1}) \approx \lambda \frac{C(V_{i-2}V_{i-1}V_i)}{C(V_{i-2}V_{i-1})} + (1-\lambda)\frac{C(V_{i-1}V_i)}{C(V_{i-1})}.$$

4. $C(V_{i-2}V_{i-1}V_i)$, $C(V_{i-2}V_{i-1})$, and $C(V_{i-1})$ respectively represent numbers of occurrence of three continuous codewords, two continuous codewords, and a single codeword; and $\lambda$ is the weight for linear adjustment.

5. $P_{catching}(V_i|V_{i-2}V_{i-1})$ is calculated in the same manner as that of $\overline{P}(V_i|V_{i-2}V_{i-1})$, except that recent data is used.

Through the above structure and method, the voice-based language ability monitoring can make up for insufficient labor for evaluation and care, assess a community interaction situation according to the number of speakers/speaking time, and detect the language ability based on the repeated similar speech segments. For dementia praecox patients, the present disclosure can be used to evaluate whether the patient starts to have a language behavior of repeated description or soliloquy. Therefore, the present disclosure not only has an economic benefit, but also can be applied to medical care for the elderly, and achieve an efficacy of assisting in evaluating whether the elderly have symptoms of dementia during home care.

The disclosure being thus described, it will be obvious that the same may be varied in many ways. Such variations are not to be regarded as a departure from the spirit and scope of the disclosure, and all such modifications as would be obvious to one skilled in the art are intended to be included within the scope of the following claims.

What is claimed is:

1. A method for awareness of language ability in a mobile device, comprising:

an audio processing step, wherein after a voice is received by a voice collection element, a voice activity detection module in a language ability evaluation unit extracts a voice segment with speech sound from the voice, and a feature extraction module in the language ability evaluation unit calculates a feature vector sequence of the voice segment, that is, extracts a voice segment feature vector for analysis;

a repeated pattern index estimating step, wherein a steady state voice segment detection and quantization module in the language ability evaluation unit directly obtains a codeword sequence, a repeated voice segment detection module in the language ability evaluation unit performs a repeated voice segment matching algorithm, so as to determine whether the codeword sequence contains one or at least one repeated voice segment, and not only a full-domain language model is established based on codewords of common daily expressions, but also a catching language model is established based on codewords that occur recently, which are used in repeated voice segment matching, so as to obtain a repeated pattern index; and a community interaction index estimating step, wherein a speaker diarization module in the language ability evaluation unit detects a speaking time/times ratio of speakers, a conversation time length, and a speaker alternation times, and even detects whether a phenomenon of soliloquy exists, so as to obtain a community interaction index;

wherein steps of the repeated voice segment matching algorithm comprises: codeword encoding for homogeneous voice segments and a codeword language model, and in the step of codeword encoding for homogeneous voice segments, voice segment division and codeword encoding are directly performed for several homogeneous voice segments on a time axis, a state number of a Semi-Hidden Markov Model (Semi-HMM) is set as 1, length features of the homogeneous voice segments are described by using a duration model, and properties of the homogeneous voice segment length are maintained through the duration model.

2. The method for awareness of language ability according to claim 1, wherein a diarization method of the speaker diarization module comprises at least one of the following methods: speaker grouping, speaker recognition and speaker identification, and a vowel triangle-based method.

3. The method for awareness of language ability according to claim 2, wherein in the vowel triangle-based method, before speaker clustering is performed, it is necessary to find a feature value of the speaker voice in a time domain or a frequency domain, quantization and modeling are performed by using a probability model such as a Gaussian mixture model (GMM) according to the feature value, and then diarization is performed.

4. The method for awareness of language ability according to claim 1, wherein the feature value is obtained by adopting formants estimation or a Mel-Frequency Cepstrum Coefficient.

5. A mobile device for awareness of language ability, comprising:

an analysis platform;

a voice collection element, electrically connected to the analysis platform, for collecting required voice data; and a language ability evaluation unit, embedded in the analysis platform, or electrically connected to the analysis platform, wherein the language ability evaluation unit receives the voice data collected by the voice collection element, evaluates and calculates a language ability, and outputs an evaluation result;

wherein the evaluation result comprises a repeated pattern index and a community interaction index;

wherein the repeated pattern index is evaluated and calculated according to one or more of the following properties: a vocabulary usage amount, a vocabulary type, and a ratio, a time point, a time length and repeated contents of a repeated voice segment, and the community interaction index is evaluated and calculated according to each of the following properties: a number of persons who speak with a user, a conversation time length, and whether the user talks alone during each time interval.

6. The mobile device for awareness of language ability according to claim 5, wherein the language ability evaluation unit at least comprises a feature extraction module, a repeated voice segment detection module, a speaker diarization module, and a vocabulary ability evaluation module.

7. The mobile device for awareness of language ability according to claim 6, wherein the feature extraction module receives the voice data input by the voice collection element, and estimates a speech parameter, comprising a frequency cepstrum coefficient, a line spectral pair coefficient, a pitch, a sound intensity, and a voice segment length; the repeated voice segment detection module detects a repeated voice segment in the voice data, outputs a voice of the repeated voice segment and calculates an occurrence ratio of the repeated voice segment, an occurrence time point, a repetition time length, or literal contents of the repeated voice segment; the speaker diarization module analyzes a speaker number, a speaking ratio of each speaker, a time length, or a speaker alternation sequence in speech data of a conversation through a speaker diarization method; and the vocabulary ability evaluation module detects and outputs a vocabulary usage amount, a vocabulary type, or a ratio, a time point, a time length or repeated contents of a repeated voice segment through vocabulary recognition or continuous speech recognition.

* * * * *